United States Patent [19]
Kleiner et al.

[11] Patent Number: 5,486,642
[45] Date of Patent: Jan. 23, 1996

[54] PROCESS FOR THE PRODUCTION OF CARBONIC ACID ESTERS

[75] Inventors: Frank-Gerald Kleiner; Robert Becker, both of Leverkusen, Germany

[73] Assignee: Bayer Aktiengesellschaft, Leverkusen, Germany

[21] Appl. No.: 410,504

[22] Filed: Mar. 24, 1995

[30]       Foreign Application Priority Data

Apr. 5, 1994 [DE] Germany .................. 44 11 668.3

[51] Int. Cl.$^6$ .................................................. C07C 68/00

[52] U.S. Cl. ........................... 558/270; 558/274; 558/277
[58] Field of Search .................................. 558/270, 274, 558/277

Primary Examiner—Johann Richter
Assistant Examiner—Michael G. Ambrose
Attorney, Agent, or Firm—Connolly & Hutz

[57]              ABSTRACT

This invention relates to a process for the production of carbonic acid esters from carbonyl compounds and organic hydroxy compounds, such as alcohols and phenols, in the presence of oxidizing metal ions.

3 Claims, No Drawings

PROCESS FOR THE PRODUCTION OF CARBONIC ACID ESTERS

This invention relates to a process for the production of carbonic acid esters from carbonyl compounds and organic hydroxy compounds such as alcohols and phenols in the presence of oxidising metal ions.

It is known that carbonic acid esters may be produced from alcohols or phenols with phosgene or chloroformic acid esters.

Organic carbonates are also obtainable by oxidative carbonylation of alcohols and phenols. Dimethyl carbonate may thus, for example, be produced by the reaction of carbon monoxide, oxygen and methanol by means of Cu(I) catalysis (see for example EP-A-0 534 545 A2). Diphenyl carbonate is obtainable by the reaction of carbon monoxide, oxygen and phenol by means of palladium(II) catalysis (see for example EP-A-0 450 442 A1). Diphenyl carbonate may also be obtained by transesterification from phenol and dimethyl carbonate (see for example WP 92 18 458). Finally, diaryl carbonates may also be produced from alkylaryl carbonates (for example JP 04 230 242).

A process for the production of carbonic acid esters has been found in which organic compounds with an X-C bond on the carbonyl carbon atom (X=H, alkyl, aryl) are reacted with metal ions having an oxidising action (towards the X-C bond) with the simultaneous presence of alkoxide and/or phenolate groups (RO- and/or PhO or bisphenolate anions).

The present invention provides a process for the production of carbonic acid esters (carbonates) by the reaction of carbonyl compounds of the formula (I)

in which

R denotes H, O—H, O—$C_1$–$C_{10}$ alkyl or O—$C_6$–$C_{10}$ aryl or O-bisphenol and X denotes H, $C_1$–$C_{10}$ alkyl, $C_6$–$C_{10}$ aryl, with metal ions (having a positive oxidation number) which cleave the C-X bond by oxidation and organic hydroxo compounds of the formula $$R\text{—OH} \qquad (II),$$

in which

R denotes $C_1$–$C_{10}$ alkyl and $C_6$–$C_{30}$ aryl, optionally under a CO (carbon monoxide) atmosphere.

The organic hydroxo compound may (for example in deprotonated form as an alkoxide) be a constituent of the metal compounds which cleave the C-X bond by oxidation.

Another starting material used for the process according to the invention comprises organic substances which may be oxidised on the carbonyl C atom.

Such organic compounds oxidisable on the carbonyl C atom may be:

formaldehyde, formic acid and the derivatives thereof (for example the $C_1$–$C_{20}$ esters, $C_6$–$C_{20}$ aromatic and $C_1$–$C_{20}$ aliphatic esters thereof) and other carboxylic acids and the derivatives thereof. Formic acid derivatives are preferred, wherein formic acid methyl ester (=methyl formate, $HCOOCH_3$) is particularly preferred.

Another starting material optionally used for the process according to the invention is carbon monoxide. It may be used in pure form or in the form of mixtures with other inert gases such as nitrogen. Although it is not a reactant (it does not appear in the reaction equation), its presence improves the yield of aromatic carbonate.

It is, moreover, sensible to use the "phenolate" reactant not only in the form of the mentioned metal compounds, but also additionally as free phenol or bisphenol.

Mixtures from which metal phenolates may arise during the reaction may also be used: for example: Cu(II) methylate and phenol (or bisphenol).

In relation to the alcohols or phenols, it may very generally be stated that any desired substituted alcohols may also be used in the process according to the invention. Phenols may, for example, also bear more than one hydroxyl group on the aromatic ring and heteromonocyclic and polycyclic aromatics may also be used.

Preferred phenolic reactants are phenols or phenolates with 6 to 30, and in particular 6 to 15 carbon atoms. According to the invention, industrially significant examples of phenolic reactants include phenol or phenolate themselves, naphthol and the anion thereof, cresols and the anions thereof, xylenols and the anions thereof and bisphenols or bisphenolates.

The phenolate reaction may be described by the following reaction equation:

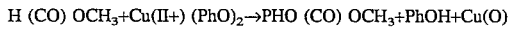

$$H(CO)OCH_3 + Cu(II+)(PhO)_2 \rightarrow PHO(CO)OCH_3 + PhOH + Cu(O)$$

(Cu(I) compounds may also occur as reaction products).

Surprisingly, the methylphenyl carbonic acid ester is highly selectively formed, while the expected formation of oligomeric oxyphenylenes largely fails to occur.

With regard to the metal compounds, the starting materials which may be used for the process according to the invention are those substances containing a metal atom or two or more metal atoms having a positive oxidation number or ionic charge number. These metal ions must be capable of reducing this positive number within a reduction/oxidation reaction with an organic substrate H-(CO)-R by accepting electrons (reduction).

Examples of such metal compounds are:

compounds with a predominantly ionic structure, which may inter alia contain metal ions, Me(n+) and alkoxide or phenolate or bisphenolate anions, such as Cu(II) (O—$C_6$–$C_{30}$ aryl)$_2$, Cu(II) (O—$C_1$–$C_{10}$ alkyl)$_2$, Cu (II) (O—$C_6$–$C_{30}$ aryl) (O—$C_1$–$C_{10}$ alkyl), compounds with complex constituents, such as K Cu(O—$C_6$–$C_{30}$ aryl)$_3$.

The cation of the compound with an ionic structure or the central ion of the complex may also be another metal ion capable of undergoing the redox reaction (such as the ions of the platinum metals of subgroup VIII of the periodic system of elements).

According to the invention, bisphenols of the formula (II) are preferably reacted

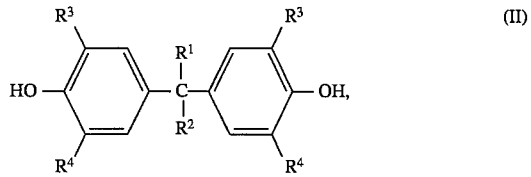

in which $R^1$ and $R^2$ mean hydrogen atoms, $C_1$–$C_4$ alkyl or phenyl residues, wherein at least one of the residues $R^3$ is a hydrogen atom and the other is a hydrogen atom or a $C_1$–$C_4$ alkyl residue and wherein at least one residue $R^4$ is a hydrogen atom and the other is a hydrogen atom or a $C_1$–$C_4$ alkyl residue.

2,2-bis(4-hydroxyphenyl) propane, which is also customarily known as "bisphenol A" (BPA), is particularly preferably used.

Phenol itself, PhOH (=$C_6H_5OH$) is also preferably used.

In general, the organic substrate which is oxidisable on the carbonyl C atom (for example the methyl formate) is added in excess, i.e. in a molar ratio relative to the phenolate (or bisphenolate) of greater than 1:1.

The process according to the invention for the production of carbonic acid esters may be operated continuously or discontinuously.

The reaction may be performed by initially introducing an excess of the organic compound oxidisable on the carbonyl C atom (which may in fact simultaneously act as a solvent) into the reaction vessel (pressure vessel, autoclave) and then stirring in the metal compound and possibly any additional free phenol or bisphenol. Finally, after establishing a CO atmosphere (pressure above atmospheric), the mixture is heated to reaction temperature while being stirred and stirring is continued until the reaction is complete.

The reaction according to the invention may be performed in the presence or absence of a solvent. In general, the oxidisable organic substrate used in excess acts as the solvent. It is, however, also possible to use inert solvents (such as chlorobenzene, chloronaphthalene or methylene chloride).

The reaction temperature for the process according to the invention may in general be between 10° and 180° C. The reaction is preferably performed between 15° and 110° C. and particularly advantageously in the range from 20° to 80° C.

The pressure must be calculated such that the presence of a liquid phase is always ensured. At reaction temperature, the pressure may generally be less than 250 bar; the reaction is preferably performed in the range between 30 and 150 bar.

EXAMPLE 1

38 g of phenol were melted under nitrogen and then mixed at 70° C. with 25 g of copper(II) methoxide in portions within 15 minutes while the mixture was stirred; the mixture was then stirred for a further 2 hours at 70° C.

The entire batch was then combined with 200 ml of methyl formate in a 0.7 liter stainless steel autoclave and adjusted to 30° C. while being stirred. CO was then introduced to a pressure of 90 bar, the temperature increased to 40° C. and the pressure adjusted to 100 bar by introducing further CO. The mixture was finally stirred for 1½ hours at 100 bar and 40° C.

The mixture was then cooled to room temperature, the autoclave depressurised, flushed with nitrogen, the reaction product discharged and analysed (GC-MS and GC).

Conversion of the phenolate (which was present in the copper phenolate which had formed in the above preliminary reaction at 70° C.) was 15% and selectivity of methylphenyl carbonate formation was in excess of 95%.

EXAMPLE 2

37 g of phenol, 25 g of copper(II) methylate and 200 ml of methyl formate were reacted in the autoclave at 100 bar CO and 60° C. for 1½ hours in accordance with the above example.

The yields and selectivities corresponded to those in the above example.

We claim:

1. Process for the production of carbonic acid esters (carbonates) by the reaction of carbonyl compounds of the formula (I)

in which

R denotes H, O—H, O—$C_1$–$C_{10}$ alkyl or O—$C_6$–$C_{10}$ aryl or O-bisphenol and X denotes H, $C_1$–$C_{10}$ alkyl, $C_6$–$C_{10}$ aryl, with metal ions (having a positive oxidation number) which cleave the C-X bond by oxidation and organic hydroxo compounds of the formula $$R—OH \qquad (II),$$

in which

R denotes $C_1$–$C_{10}$ alkyl and $C_6$–$C_{30}$ aryl, optionally under a CO (carbon monoxide) atmosphere.

2. Process according to claim 1, characterised in that methyl formate ($HCOOCH_3$) is used as the carbonyl compound.

3. Process according to claim 1, characterised in that $Cu^{2+}$ is used as the metal ion which cleaves by oxidation.

* * * * *